United States Patent
Chang (10) Patent No.: US 9,411,070 B2
(45) Date of Patent: Aug. 9, 2016

(54) EXTENDABLE WIRELESS SOIL MEASUREMENT APPARATUS

(71) Applicant: Cheng-Hung Chang, Hsinchu (TW)

(72) Inventor: Cheng-Hung Chang, Hsinchu (TW)

( * ) Notice: Subject to any disclaimer, the term of this patent is extended or adjusted under 35 U.S.C. 154(b) by 425 days.

(21) Appl. No.: 14/105,799

(22) Filed: Dec. 13, 2013

(65) Prior Publication Data

US 2015/0168594 A1     Jun. 18, 2015

(51) Int. Cl.
 *G01V 9/00* (2006.01)
 *A01G 25/16* (2006.01)
 *G01N 33/24* (2006.01)
 *A01C 21/00* (2006.01)

(52) U.S. Cl.
 CPC ............... *G01V 9/00* (2013.01); *A01G 25/167* (2013.01); *A01C 21/007* (2013.01); *G01N 2033/245* (2013.01)

(58) Field of Classification Search
 None
 See application file for complete search history.

(56) References Cited

U.S. PATENT DOCUMENTS

| | | | |
|---|---|---|---|
| 4,492,111 A * | 1/1985 | Kirkland | 73/84 |
| 6,317,694 B1 * | 11/2001 | Kram et al. | 702/11 |
| 6,975,245 B1 * | 12/2005 | Slater et al. | 340/870.16 |
| 7,201,060 B2 * | 4/2007 | Frost et al. | 73/784 |
| 7,788,970 B2 * | 9/2010 | Hitt et al. | 73/73 |

FOREIGN PATENT DOCUMENTS

FR        2825153        * 11/2002

* cited by examiner

Primary Examiner — Robert R Raevis
(74) Attorney, Agent, or Firm — Rabin & Berdo, P.C.

(57) ABSTRACT

A two-tier wireless soil measurement apparatus is disclosed, including a top head and a plurality of sensors, wherein the top head being placed on or above the ground and the plurality of sensors being buried under the soil for sensing soil conditions, generating soil data representing the sensed soil conditions, and transmitting generated soil conditions to the top head; the plurality of sensors able to be assembled into a pole and each of the plurality of sensors including a sensor unit for sensing a soil condition; a circuit module connected to the sensor unit for transmitting sensed soil condition to the top head, a sensor housing for housing the sensor unit and the circuit module; and an engaging element for engaging two sensors in a head-to-tail manner for form a pole.

9 Claims, 7 Drawing Sheets

EXTENDABLE WIRELESS SOIL MEASUREMENT APPARATUS

FIELD OF THE INVENTION

The present invention generally relates to an extendable wireless soil measurement apparatus for monitoring sub-surface soil conditions.

BACKGROUND OF THE INVENTION

Figure 1:
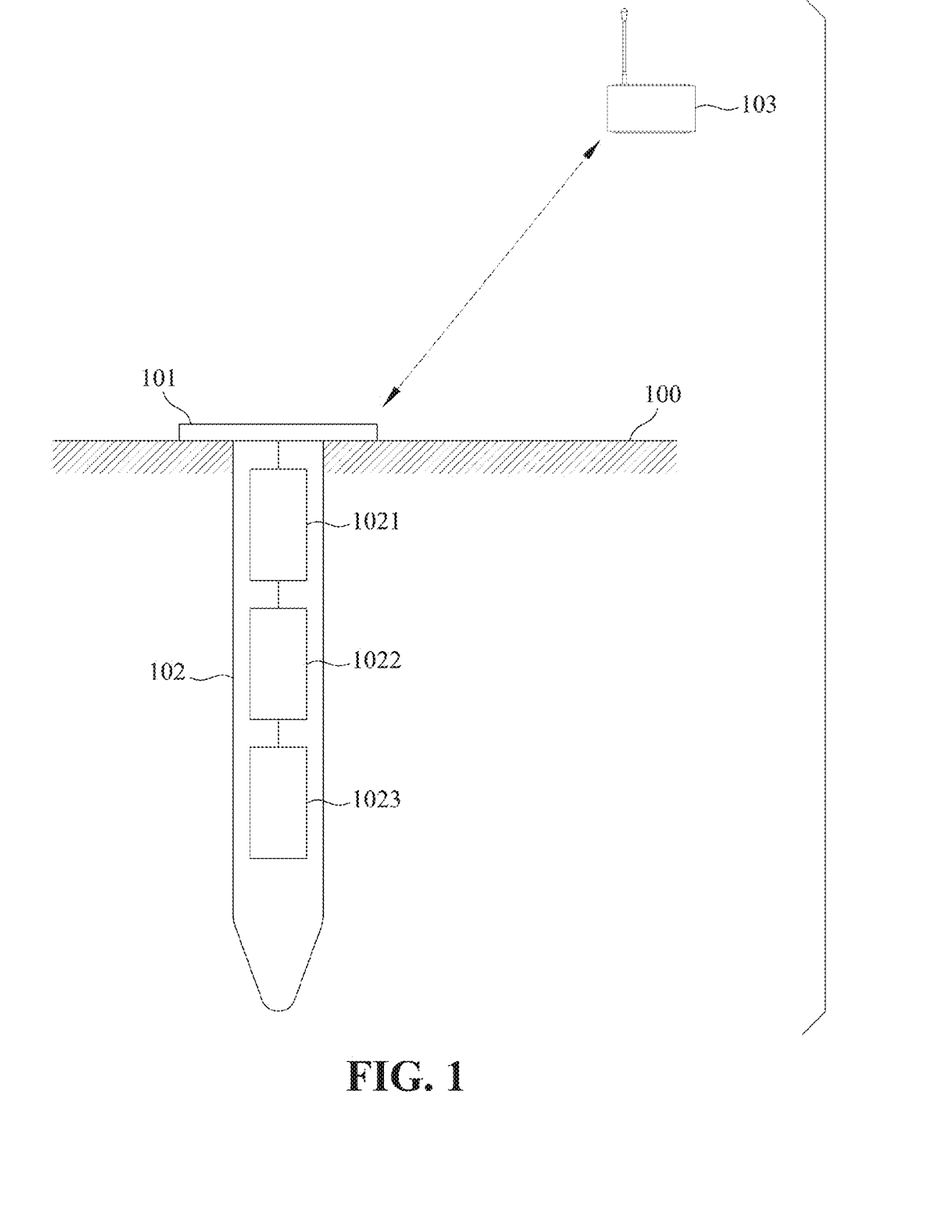
FIG. 1 shows a schematic view of a conventional wireless soil sensor probe.

The wireless soil sensors are often used to reduce water waste and water produce effectively through continuous monitoring of the soil moisture level as well as other soil conditions. The conventional wireless soil sensor system uses a probe buried into the soil. FIG. 1 shows a schematic view of a conventional wireless soil sensor probe. As shown in FIG. 1, a wireless soil sensor probe includes a top part 101 and a shaft part 102. The shaft part 102 is usually made in a tubular shape to house a plurality of sensors 1021, 1022, 1023, as shown in FIG. 1. The sensors 1021, 1022, 1023 monitor various soil conditions, such as, moisture, specific compounds, and so on, and pass the monitored data through a circuit to the top part 101. The top part 101 is exposed above the soil level 100 to transmit collected soil information to a data station 103.

The conventional wireless soil sensor probe shows certain practical disadvantages when deployed. For example, when considering a large-area field deployment of the wireless soil sensor probes, a large number of probes must be used. As the large-area field may include various soil conditions in different parts of the field, different soil conditions may be required to be monitored at different parts. However, as the shaft part 102 in the conventional wireless soil sensor probe is often of fixed length, and the soil sensor probes usually include same sensor unit 1021, 1022, 1023 across the probes, the inflexibility may increase the cost and difficulty of deployment.

SUMMARY OF THE INVENTION

The present invention has been made to overcome the above-mentioned drawback of conventional wireless soil sensor system. The primary object of the present invention is to provide an extendable wireless soil measurement apparatus that provides flexibility and ease for deployment.

An exemplary embodiment of the present invention discloses an extendable wireless soil measurement apparatus, including a top head and a plurality of sensors, wherein the top head being placed on or above the ground and the plurality of sensors being buried under the soil for sensing soil conditions, generating soil data representing the sensed soil conditions, and transmitting generated soil conditions to the top head; the plurality of sensors able to be assembled into a pole and each of the plurality of sensors including a sensor unit for sensing a soil condition; a circuit module connected to the sensor unit for transmitting sensed soil condition to the top head, a sensor housing for housing the sensor unit and the circuit module; and an engaging element for engaging two sensors in a head-to-tail manner for form a pole.

The foregoing and other objects, features, aspects and advantages of the present invention will become better understood from a careful reading of a detailed description provided herein below with appropriate reference to the accompanying drawings.

BRIEF DESCRIPTION OF THE DRAWINGS

The present invention can be understood in more detail by reading the subsequent detailed description in conjunction with the examples and references made to the accompanying drawings, wherein.

DETAILED DESCRIPTION OF THE PREFERRED EMBODIMENTS

Figure 2:
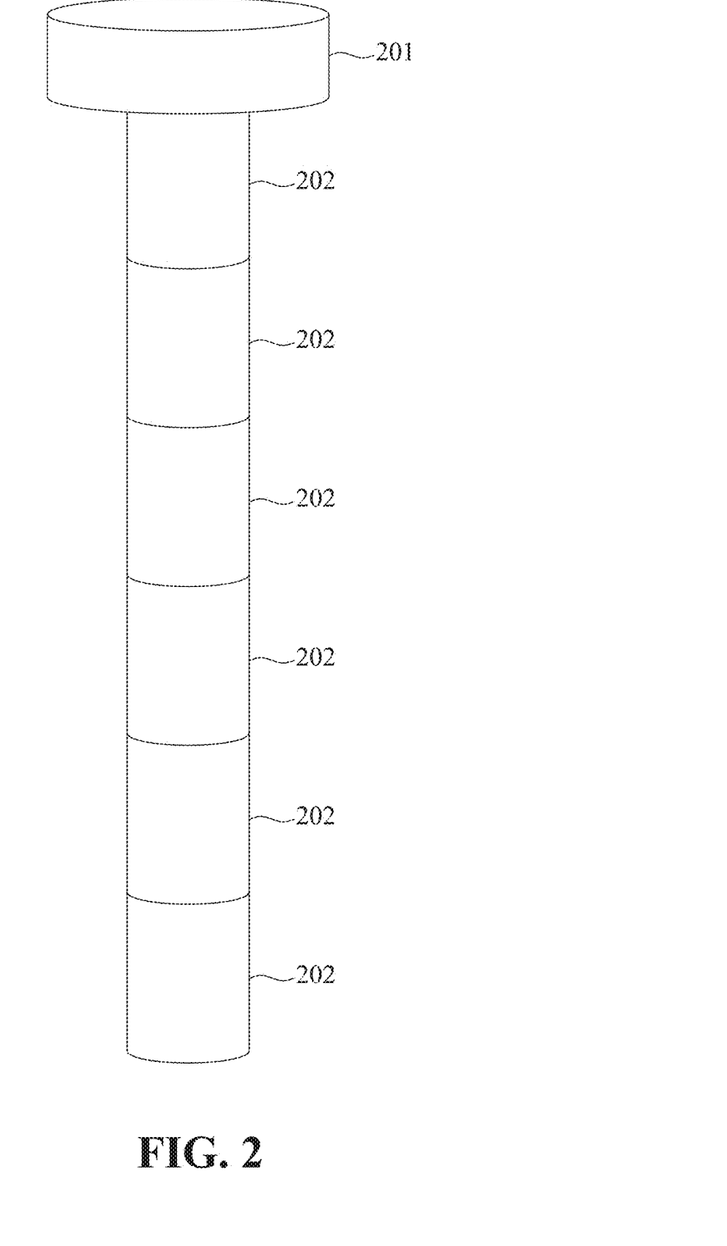
FIG. 2 shows a schematic view of an extendable wireless soil measurement apparatus according to an embodiment of the present invention.

FIG. 2 shows a schematic view of an extendable wireless soil measurement apparatus according to an embodiment of the present invention. As shown in FIG. 2, the extendable wireless soil measurement apparatus includes a top head 201 and at least a sensor 202. In the present embodiment, six sensors are shown. The top head 201 is placed on or above the ground (i.e., soil surface) for transmitting data collected from the plurality of sensors to a remote data station through a wireless means. The six sensors 202 are assembled into a post for burying under the soil. Each sensor is able to sense a soil condition, generate soil data representing the sensed soil condition, and transmit generated soil data to the top head. The transmission between the sensors 202 and the top head 201 may be either through a wired means or a wireless means. In the present embodiment, a wireless means is depicted.

It should be noted that the sensors 202 may be the same or different from each other. In other words, the sensors 202 may be used to monitor the same soil condition at different depths, or different soil conditions at the same depth. This provides more flexibility for various applications.

Figure 3:
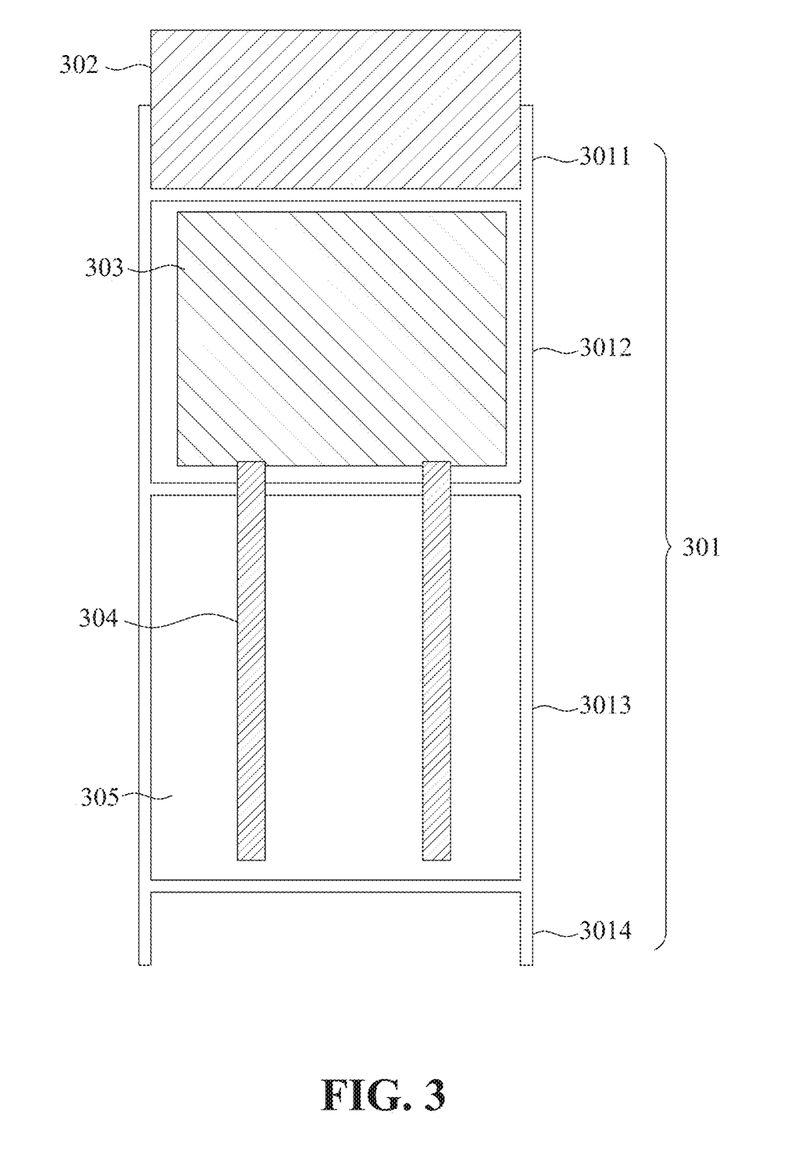
FIG. 3 shows a schematic cross-sectional view of the structure of the sensor according to an embodiment of the present invention.

FIG. 3 shows a schematic cross-sectional view of the structure of the sensor according to an embodiment of the present invention. As shown in FIG. 3, the sensor further includes a sensor housing 301, an engaging element 302, a circuit module 303 and a sensor unit 304. The sensor housing 301 further includes a first segment 3011, a second segment 3012, a third segment 3013 and a fourth segment 3014, wherein the four segments may be connected together to form an integrated shell of a cylindered shape. The sensor housing 301 is preferably made of metal, porous ceramic or plastic material. The first segment 3011 is structured to include a cylindered wall and a bottom to form a dish to fit the engaging element 302 in. The second segment 3012 is also structured to include a cylindered wall and a bottom. When connected, the bottom of the first segment 3011 and the second segment 3012 form a cavity for housing the circuit module 303 to seal and protect the circuit module 303 from contacting the soil. The bottom has an opening for allowing the sensor unit 304 to extend into the cavity housing the circuit module 303 and connected electrically to the circuit module 303. The third segment 3013 has a structure similar to the first segment 3011, except that a plurality of opening is disposed on the cylindered wall. When connected to the second segment 3012, a cavity is formed for housing the sensor unit 304. The sensor unit 304 must tightly fit the opening at the bottom of the second segment 3012 to ensure a sealed cavity formed by the second segment 3012 and the bottom of the first segment 3011. The soil is allowed to enter the openings on the wall of the third segment to fill the cavity and contact the sensor. The fourth segment 3014 is structured as a cylindered wall attached to the bottom of the third segment 3013, and may be considered as an extension of the third segment 3013. When two sensors 202 are assembled, the fourth segment 3014 of the previous sensor 202 and the first segment 3011 of the next sensor 202 are engaged by the engaging element 302. As such, the sensors can be connected head-to-tail through engaging elements 302 to form a pole.

It should be noted that sensor unit 304 and the circuit module 303 can sense a condition of the soil, generate soil data representing the soil condition and transmit the soil data to the top head. Furthermore, in the present embodiment, the sensor unit 304 may be an accelerometer, a soil tension meter, a soil moisture sensor, a soil temperature sensor, a soil dissolved oxygen sensor, a soil pH level sensor, a soil conductivity sensor, a soil dielectric frequency sensor, or any combination of the above to monitor any necessary combination soil conditions.

Figure 4:
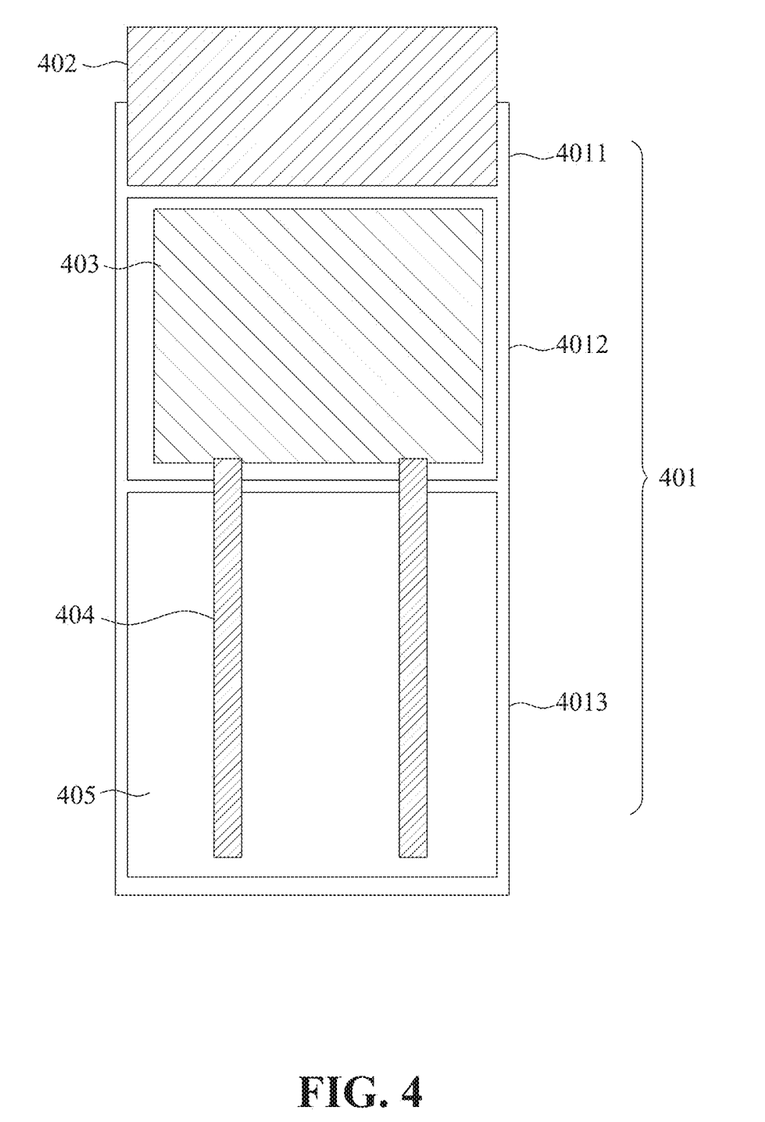
FIG. 4 shows a schematic cross-sectional view of the structure of the sensor according to another embodiment of the present invention.

FIG. 4 shows a schematic cross-sectional view of the structure of the sensor according to another embodiment of the present invention. This embodiment is similar to the embodiment in FIG. 3, except that the sensor housing 401 does not include a fourth segment. As such, this embodiment can be used as a terminal sensor in a cascaded pole of sensors 202.

Figure 5:
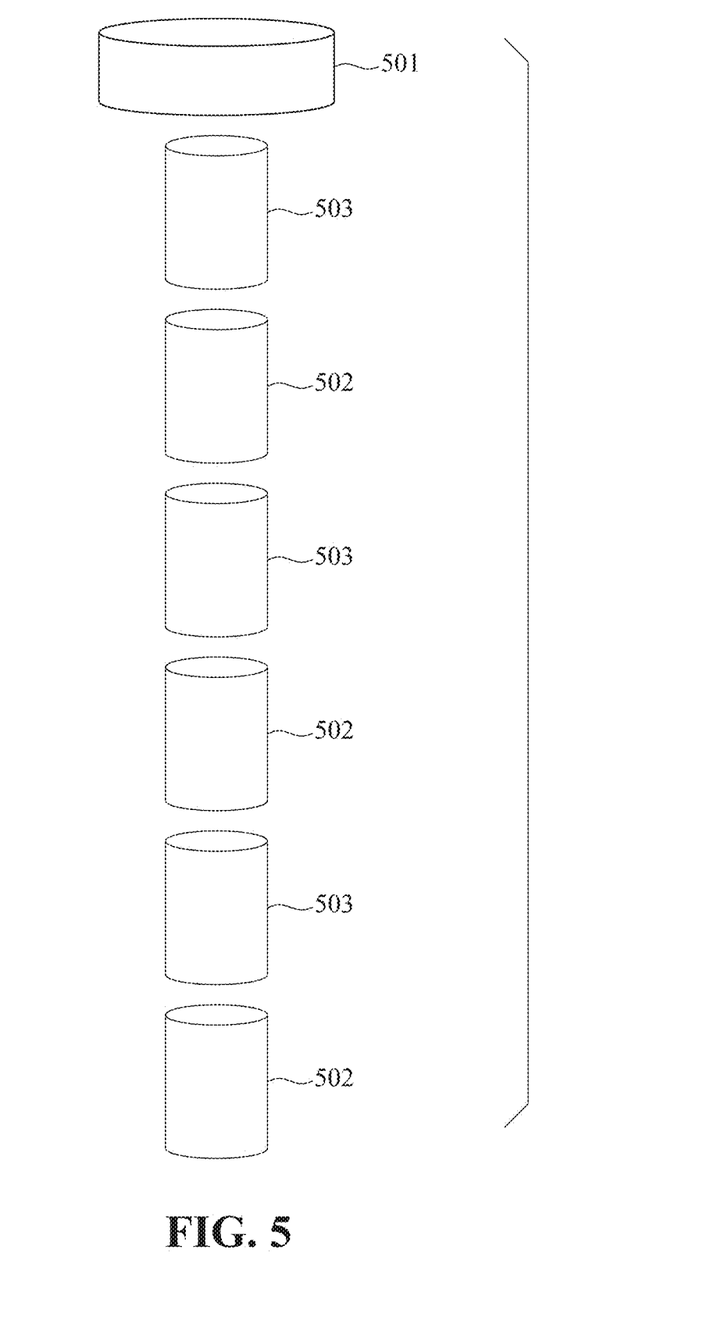
FIG. 5 shows a schematic view of an extendable wireless soil measurement apparatus according to another embodiment of the present invention.

Furthermore, as the pole length of assembled sensors 202 may not always match the required burial depth for soil monitoring, an extension connector may be further disposed to extend the pole length or adjust the depth of the sensors under the soil. FIG. 5 shows a schematic view of an extendable wireless soil measurement apparatus according to another embodiment of the present invention. As shown in FIG. 5, the present embodiment further includes a plurality of connectors 503, with a connector is disposed between two sensors 502, and between the top head 501 and the sensor 502 to form the pole. The structure of the connector 503 includes the same engaging mechanism used in the sensor 502 for engagement. As such, the connector 503 and the sensor 502 may also be engaged in the same head-to-tail manner to form the pole.

Figure 6:
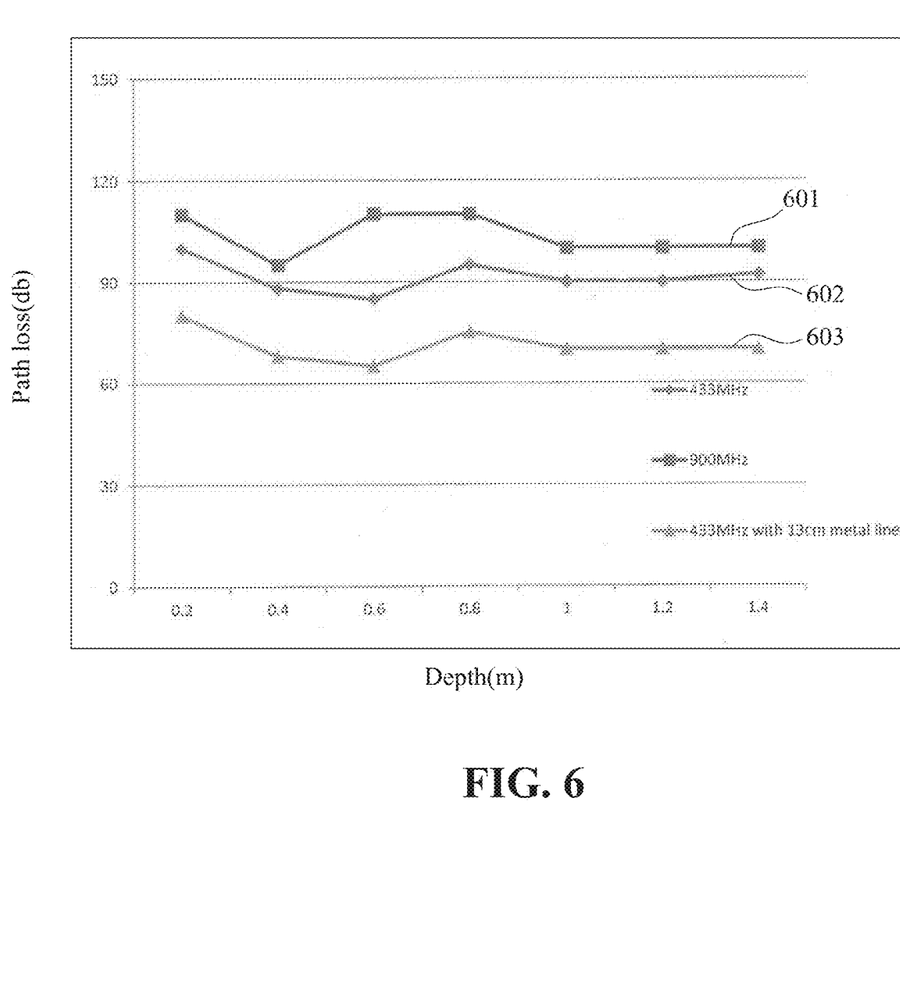
FIG. 6 shows a diagram of the propagation loss of wireless signal for different frequencies according to the present invention.

An additional benefit for disposing connectors 503 to form the pole is that the length of the sensor 502 and the connector 503 may also be adjusted to achieve optimal performance of the sensing and data transmission. For example, in the present embodiment, when the sensor 502 uses wireless communication means, say, at a frequency of 433 MHz, to communicate data with the head top 501 in this embodiment, the preferred lengths of the sensor 502 and the connector 503 are 17 cm and 13 cm, respectively, to achieve better performance according to experiment data. FIG. 6 shows a diagram of the propagation loss of wireless signal for different frequencies according to the present invention. As shown in FIG. 6, the line 601 indicates the signal loss at frequency 900 MHz versus depth of the soil, and the line 602 shows the signal loss at frequency 433 HMz. The line 603 shows the propagation loss at 433 MHz for a metal line of length 13 cm. Hence, the connector may further include a metal line of 13 cm in length to reduce the wireless signal propagation through the connector.

It should be noted that the top head 201 may further include one or more sensor units (not shown), for sensing various soil surface conditions, such as, air humidity level, air temperature, light level, $CO_2$ level, air pressure and so on.

Figure 7:
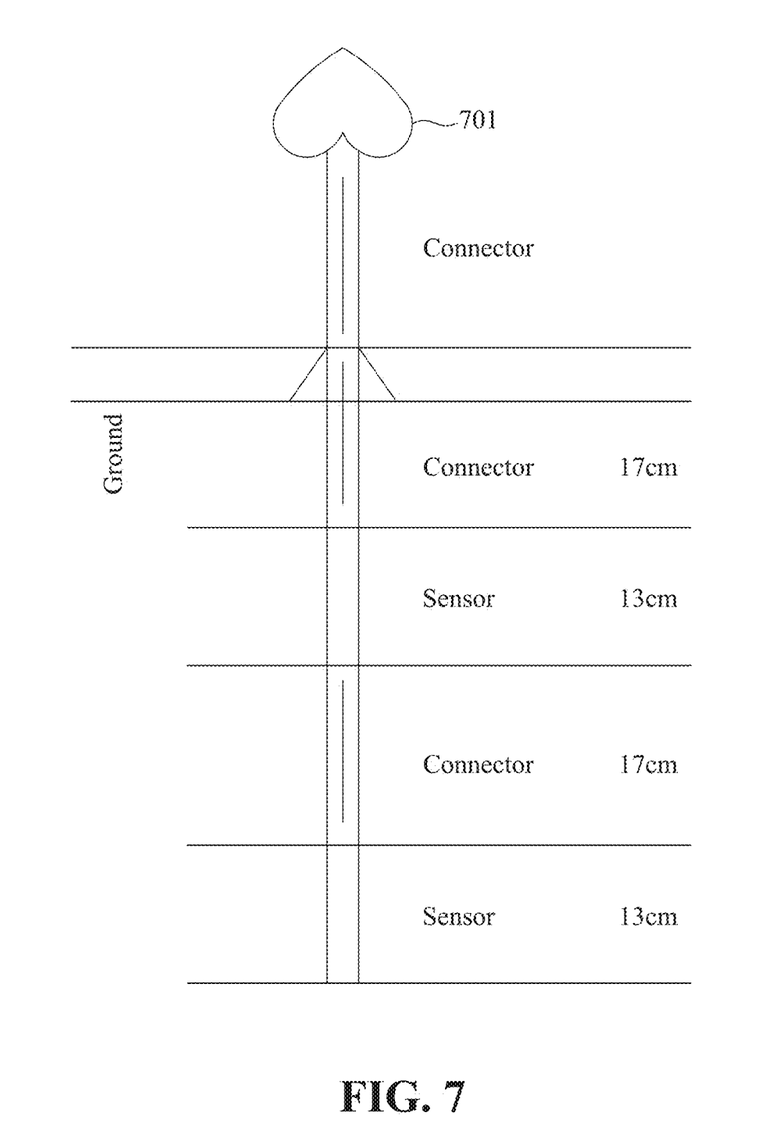
FIG. 7 shows a schematic view of the extendable soil measurement apparatus in actual application according to the present invention.

FIG. 7 shows a schematic view of the extendable soil measurement apparatus in actual application according to the present invention. As shown in FIG. 7, the top head 701 of this embodiment has a heart-shape shell. The appearance of the top head 701 may vary to increase visual esthetics of the apparatus of the invention to provide decorative function or easy for visual searching and locating when a GPS sensor is not included. On the other hand, when solar power is used, the solar cell may be used to form the shell of the top head.

In summary, the extendable wireless soil measurement apparatus of the present invention uses a plurality of sensors and/or a plurality of connectors to form the pole so as to provide ease and flexibility of the deployment of the sensors to accommodate the various underground conditions.

Although the present invention has been described with reference to the preferred embodiments, it will be understood that the invention is not limited to the details described thereof. Various substitutions and modifications have been suggested in the foregoing description, and others will occur to those of ordinary skill in the art.

Therefore, all such substitutions and modifications are intended to be embraced within the scope of the invention as defined in the appended claims.

What is claimed is:

1. An extendable wireless soil measurement apparatus, comprising:
    a top head, disposed above a soil surface for transmitting data to a data station through a wireless means; and
    a plurality of sensors, disposed under soil for sensing soil conditions, generating soil data representing the sensed soil conditions, and transmitting generated soil conditions to the top head, the plurality of sensors able to be assembled into a pole;
    wherein each of the plurality of sensors further comprising:
    a sensor unit for sensing a soil condition and generating soil data representing the sensed soil condition;
    a circuit module connected to the sensor unit for transmitting generated soil data to the top head
    a sensor housing for housing the sensor unit and the circuit module; and
    an engaging element for engaging two sensors in a head-to-tail manner to form a pole,
    wherein the apparatus further comprises at least a connector, the connector being disposed between sensors or between the sensor and the top head to adjust the pole length and the depth of the sensors when the apparatus is buried under soil, and
    the connector further comprises a metal line for reducing wireless transmission loss through the connector.

2. The apparatus as claimed in claim 1, wherein the sensor housing preferably made of metal, porous ceramic or plastic material.

3. The apparatus as claimed in claim 2, wherein the sensor housing further comprises:
    a first segment, further comprising a cylindered wall and a bottom, to form a dish to fit the engaging element in;
    a second segment, further comprising a cylindered wall and a bottom, connected to the bottom of the first segment to form a cavity for housing the circuit module to seal and protect the circuit module from contacting the soil, the bottom having an opening for allowing the sensor unit to extend into the cavity housing the circuit module and to connect electrically to the circuit module;
    a third segment, further comprising a cylindered wall and a bottom, connected to the second segment to form a cavity housing the sensor unit, the cylindered wall is disposed with a plurality of openings to allow the soil to enter the openings on the cylindered wall of the third segment to fill the cavity and contact the sensor, the sensor unit fitting tightly to the opening disposed at the bottom of the second segment to ensure a sealed cavity formed by the second segment and the bottom of the first segment; and a fourth segment, comprising a cylindered wall, attached to the bottom of the third segment;

wherein the four segments being connected together to form an integrated shell of a cylindered shape, and when two sensors being assembled, the fourth segment of one sensor and the first segment of the other sensor being engaged by the engaging element in a head-to-tail manner to form a pole.

4. The apparatus as claimed in claim 1, wherein the length of the metal line can be adjusted based on a wireless transmission frequency used for transmitting soil data from the sensor to the top head.

5. The apparatus as claimed in claim 4, wherein the metal line is 13 cm long when the wireless transmission frequency is 433 MHz.

6. An extendable wireless soil measurement apparatus, comprising:

a top head, disposed above a soil surface for transmitting data to a data station through a wireless means; and a plurality of sensors, disposed under soil for sensing soil conditions, generating soil data representing the sensed soil conditions, and transmitting generated soil conditions to the top head, the plurality of sensors able to be assembled into a pole;

wherein each of the plurality of sensors further comprises:

a first sensor unit for sensing a soil condition and generating soil data representing the sensed soil condition;

a circuit module connected to the first sensor unit for transmitting generated soil data to the top head a sensor housing for housing the first sensor unit and the circuit module; and an engaging element for engaging two sensors in a head-to-tail manner to form a pole, wherein the top head further comprises one or more second sensor units.

7. The apparatus as claimed in claim 6, wherein each first or second sensor unit may be an air humidity level sensor, an air temperature sensor, a light level sensor, a $CO_2$ level sensor, an air pressure sensor, a GPS sensor, an accelerometer or any combination of the above.

8. An extendable wireless soil measurement apparatus, comprising:

a top head, disposed above a soil surface for transmitting data to a data station through a wireless means; and a plurality of sensors, disposed under soil for sensing soil conditions, generating soil data representing the sensed soil conditions, and transmitting generated soil conditions to the top head, the plurality of sensors able to be assembled into a pole;

wherein each of the plurality of sensors further comprises:

a sensor unit for sensing a soil condition and generating soil data representing the sensed soil condition;

a circuit module connected to the sensor unit for transmitting generated soil data to the top head a sensor housing for housing the sensor unit and the circuit module; and an engaging element for engaging two sensors in a head-to-tail manner to form a pole, wherein said sensor unit can be an accelerometer, a soil tension meter, a soil moisture sensor, a soil temperature sensor, a soil dissolved oxygen sensor, a soil pH level sensor, a soil conductivity sensor, a soil dielectric frequency sensor, or any combination of the above.

9. An extendable wireless soil measurement apparatus, comprising:

a top head, disposed above a soil surface for transmitting data to a data station through a wireless means; and a plurality of sensors, disposed under soil for sensing soil conditions, generating soil data representing the sensed soil conditions, and transmitting generated soil conditions to the top head, the plurality of sensors able to be assembled into a pole;

wherein each of the plurality of sensors further comprises:

a sensor unit for sensing a soil condition and generating soil data representing the sensed soil condition;

a circuit module connected to the sensor unit for transmitting generated soil data to the top head a sensor housing for housing the sensor unit and the circuit module; and an engaging element for engaging two sensors in a head-to-tail manner to form a pole, wherein the sensor housing is made of metal, porous ceramic or plastic material, wherein the sensor housing further comprises:

a first segment, further comprising a cylindered wall and a bottom, to form a dish to fit the engaging element in;

a second segment, further comprising a cylindered wall and a bottom, connected to the bottom of the first segment to form a cavity for housing the circuit module to seal and protect the circuit module from contacting the soil, the bottom having an opening for allowing the sensor unit to extend into the cavity housing the circuit module and to connect electrically to the circuit module;

a third segment, further comprising a cylindered wall and a bottom, connected to the second segment to form a cavity housing the sensor unit, the cylindered wall is disposed with a plurality of openings to allow the soil to enter the openings on the cylindered wall of the third segment to fill the cavity and contact the sensor, the sensor unit fitting tightly to the opening disposed at the bottom of the second segment to ensure a sealed cavity formed by the second segment and the bottom of the first segment; and a fourth segment, comprising a cylindered wall, attached to the bottom of the third segment;

wherein the four segments being connected together to form an integrated shell of a cylindered shape, and when two sensors being assembled, the fourth segment of one sensor and the first segment of the other sensor being engaged by the engaging element in a head-to-tail manner to form a pole.

* * * * *